United States Patent [19]
Golub et al.

[11] Patent Number: 6,015,804
[45] Date of Patent: Jan. 18, 2000

[54] METHOD OF USING TETRACYCLINE COMPOUNDS TO ENHANCE INTERLEUKIN-10 PRODUCTION

[75] Inventors: Lorne M. Golub, Smithtown; Christopher T. Ritchlin, Canandaigua; Robert A. Greenwald, Melville; Sally Haas-Smith, Penfield; Susan A. Moak, Bayside; Hsi-Ming Lee, Setauket, all of N.Y.

[73] Assignees: The Research Foundation of State University of New York, Albany; University of Rochester, Rochester, both of N.Y.

[21] Appl. No.: 09/151,534

[22] Filed: Sep. 11, 1998

[51] Int. Cl.$^7$ .................................................. A61K 31/65
[52] U.S. Cl. ............................................. 514/152
[58] Field of Search ............................................. 514/152

[56] References Cited

U.S. PATENT DOCUMENTS

| | | | |
|---|---|---|---|
| 4,704,383 | 11/1987 | McNamara et al. ..................... | 514/152 |
| 5,368,854 | 11/1994 | Rennick ................................. | 424/85.2 |
| 5,532,227 | 7/1996 | Golub et al. ........................... | 514/152 |
| 5,650,396 | 7/1997 | Carlino et al. . | |
| 5,665,345 | 9/1997 | Yarchoan et al. . | |
| 5,726,156 | 3/1998 | Girten et al. . | |

OTHER PUBLICATIONS

Donna Rennick, Dan Berg and Gina Holland, "Interleukin 10: An Overview", *Progress in Growth Factor Research*, vol 4. pp. 207, 219–221, 1992.

P. D'Agostino, M. LaRosa, C. Barbera, F. Arcolco, G. DiBella, S. Milano and E. Cillari, "Doxycycline Reduces Morality to Lethal Endotoxemia by Reducing Nitric Oxide Synthesis via an Interleukin–10–Independent Mechanism", *The Journal of Infectious Diseases*, 177:489–492, 1998.

M. Stearns, K. Fudge, F. Garcia and M. Wang, "IL–10 Inhibition of Human Prostate PC–3 ML Cell Metastases in SCID Mice: IL–10 Stimulation of TIMP–1 and Inhibition of MMP–2/MMP–9 Expression", *Invasion and Metastasis*, 17:62–74, 1997.

A.S.Y. Ho and K. Moore, "Interleukin–10 and its receptor", *Therapeutic Immunology*, 1:173, 1994.

K. Pennline, E. Gaffney and M. Monahan, "Recombinant Human IL–10 Prevents the Onset of Diabetes in the Non-obese Diabetic Mouse", *Clinical Immunology and Immunopathyology*, vol. 71, No. 2 p. 169, 1994.

C. Jorgensen, F. Apparailly, I. Couret, F. Canovas, C. Jacquet and J. Sany, "Interleukin–4 and interleukin–10 are chondroprotective and decrease mononuclear cell recruitment in human rheumatoid synovium in vivo", *Immunology*, 93:518, 1998.

B. Balasa and Nora Sarvetnick, "The Paradoxical Effects of Interleukin 10 in the Immunoregulation of Autoimmune Diabetes", *Journal of Autoimmunity*, 9:283, 1996.

W. Krenger and J. Ferrara, "Graft–versus–Host Disease and the Th1/Th2 Paradigm", *Immunologic Research*, 15:50, 1996.

C. Ritchlin, S. Smith, D. Hicks, J. Cappuccio, C. Osterland and R. Looney, "Patterns of Cytokine Production in Psoriatic Synovium", *The Journal of Rheumatology*, 25:1544–1552, 1998.

*Primary Examiner*—James H. Reamer
*Attorney, Agent, or Firm*—Hoffmann & Baron, LLP

[57] ABSTRACT

The invention is a method of enhancing endogenous interleukin-10 production in mammalian cells and tissues, which includes administering an effective amount of a tetracycline derivative. The method also includes enhancing interleukin-10 production by administering an effective amount of the tetracycline derivative to a mammal. Preferred tetracycline compounds are tetracycline compounds which have been modified to reduce or eliminate their antimicrobial activity. The method can be used to treat medical conditions in mammals characterized by excessive IL-1 and TNF α production.

21 Claims, 5 Drawing Sheets

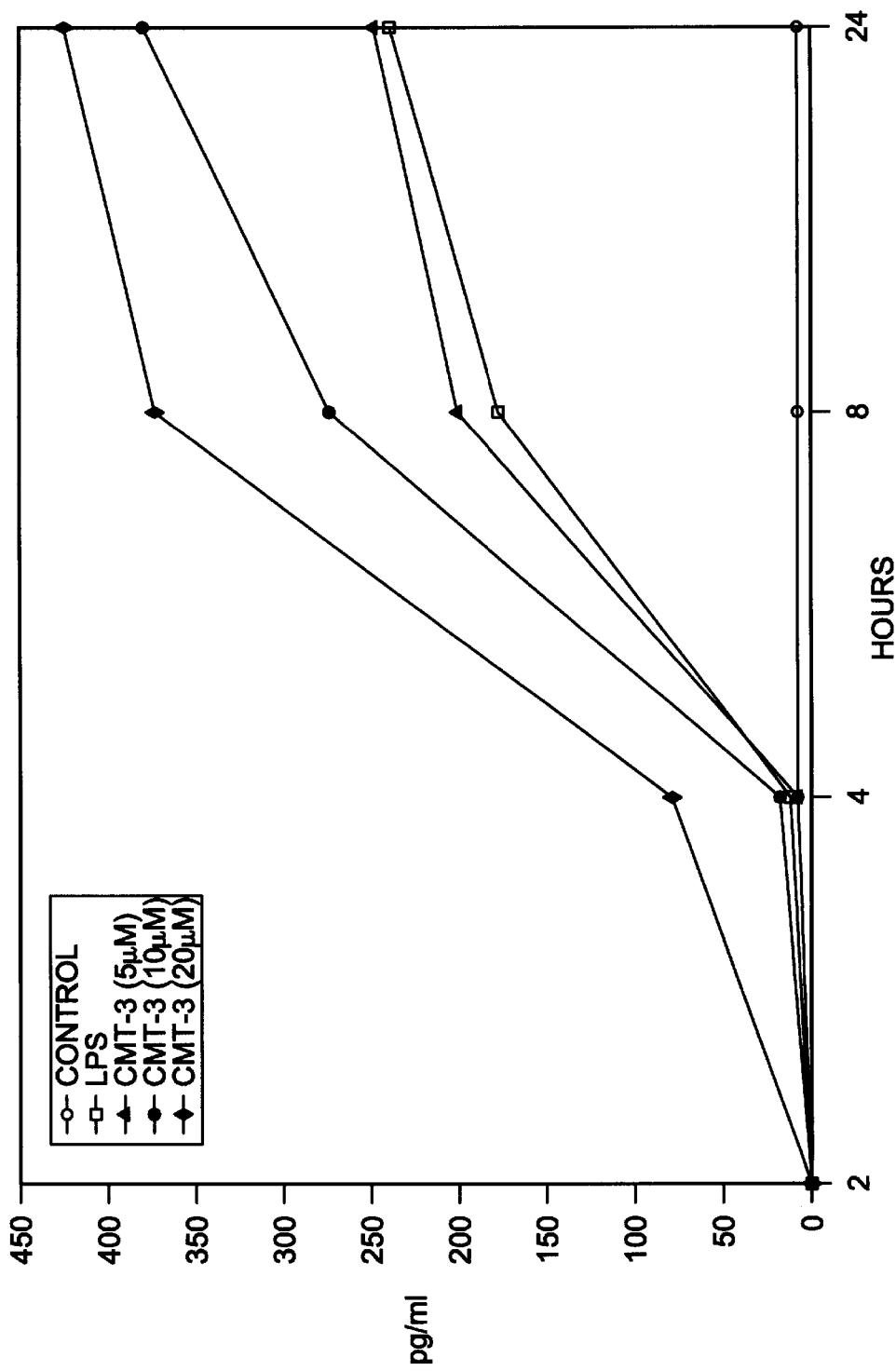

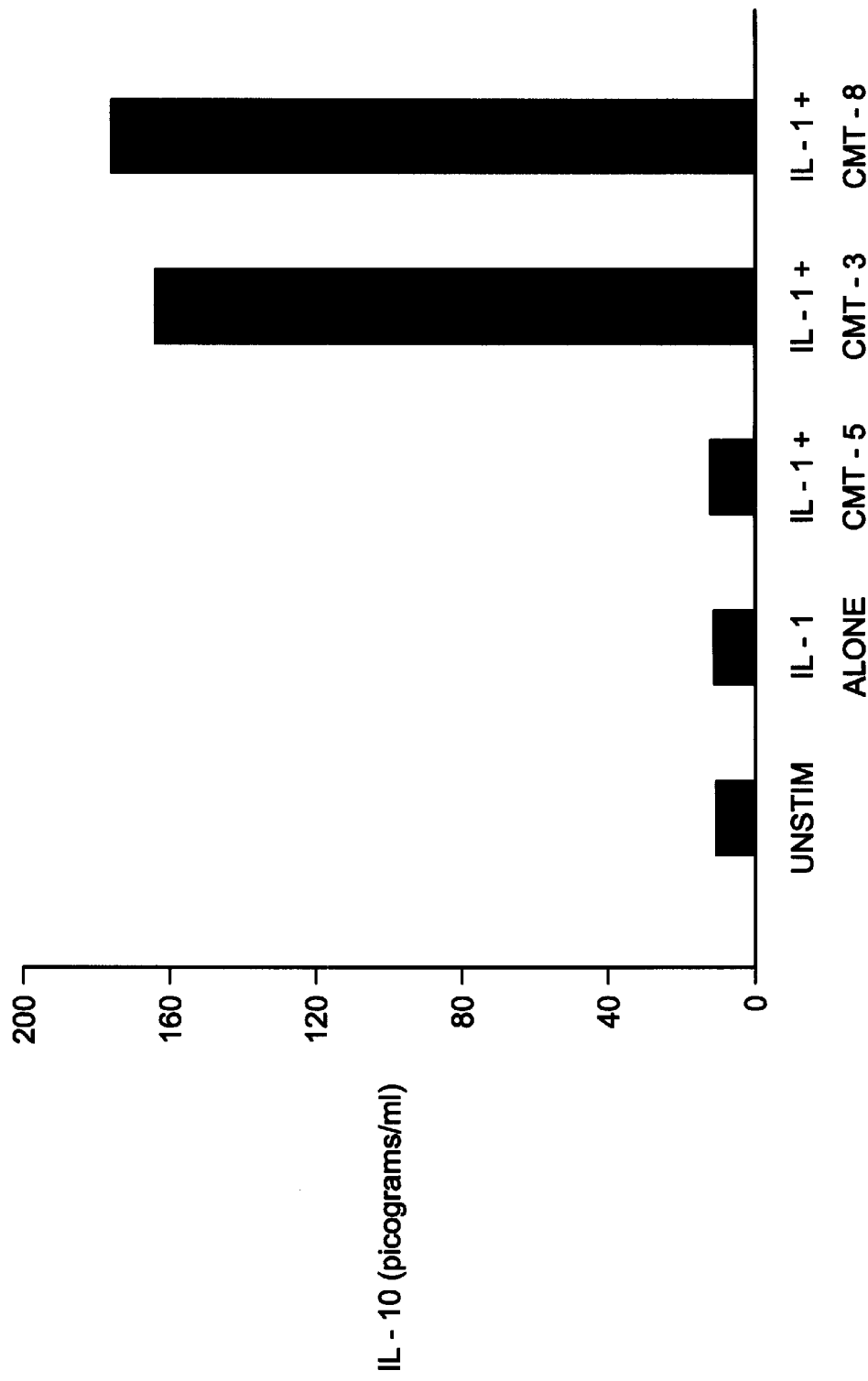

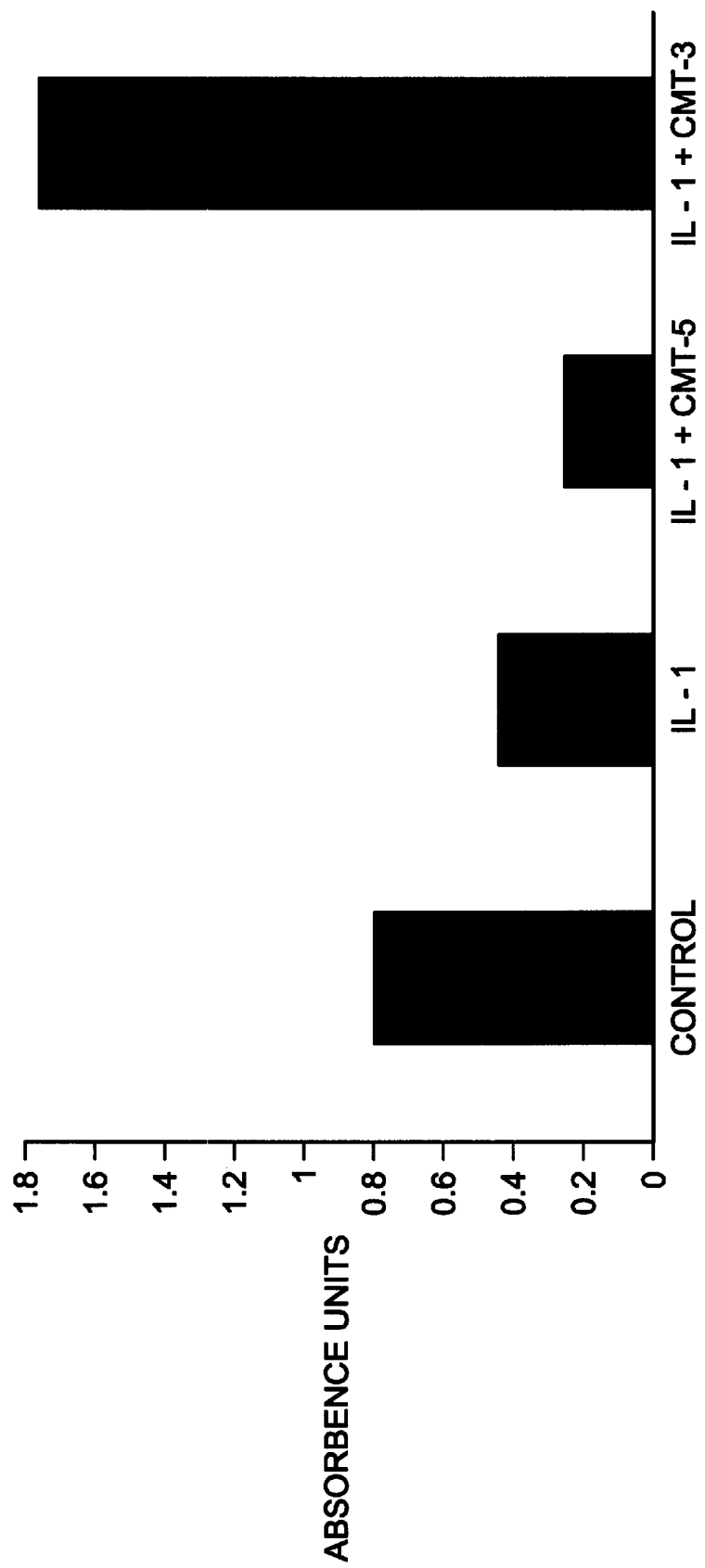

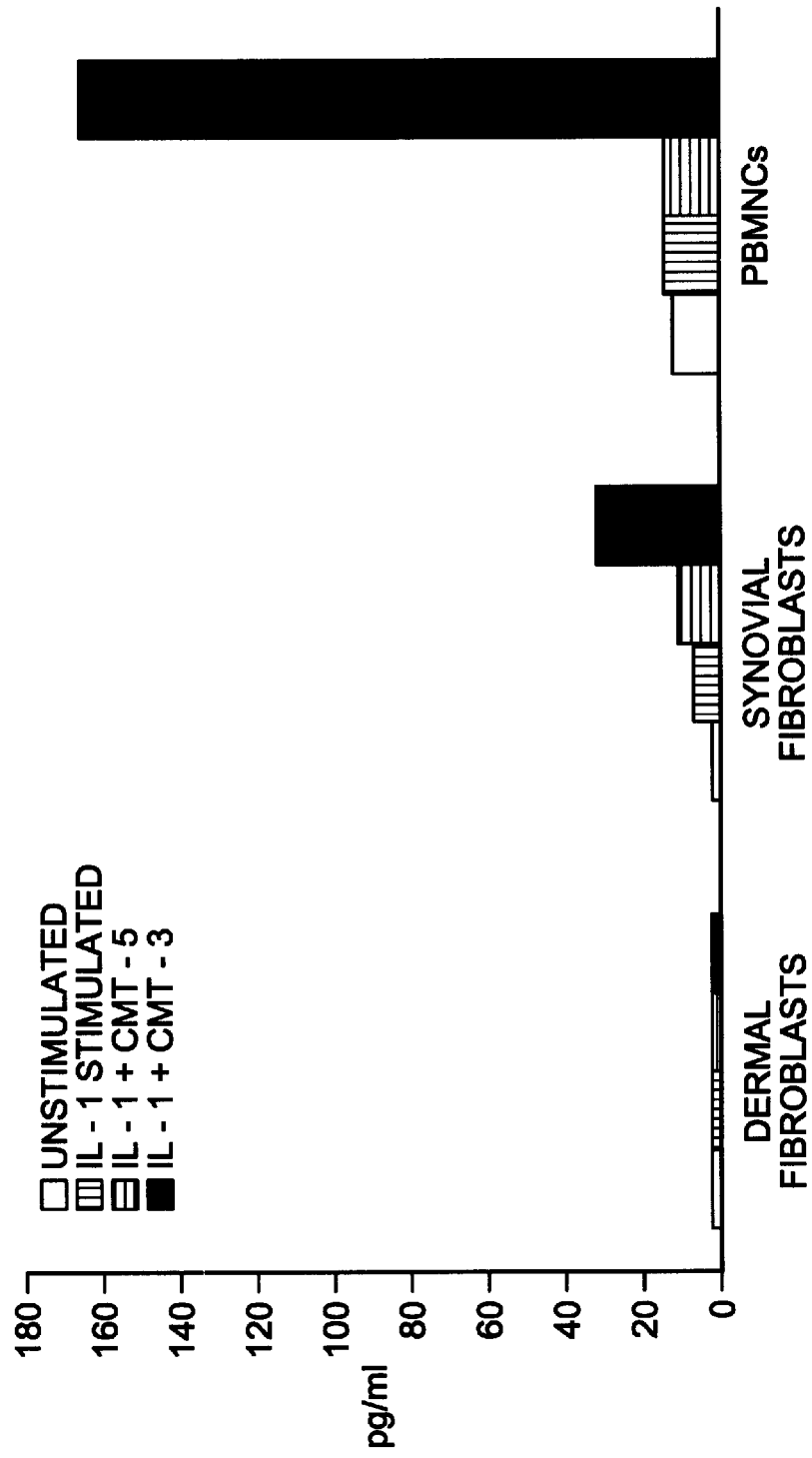

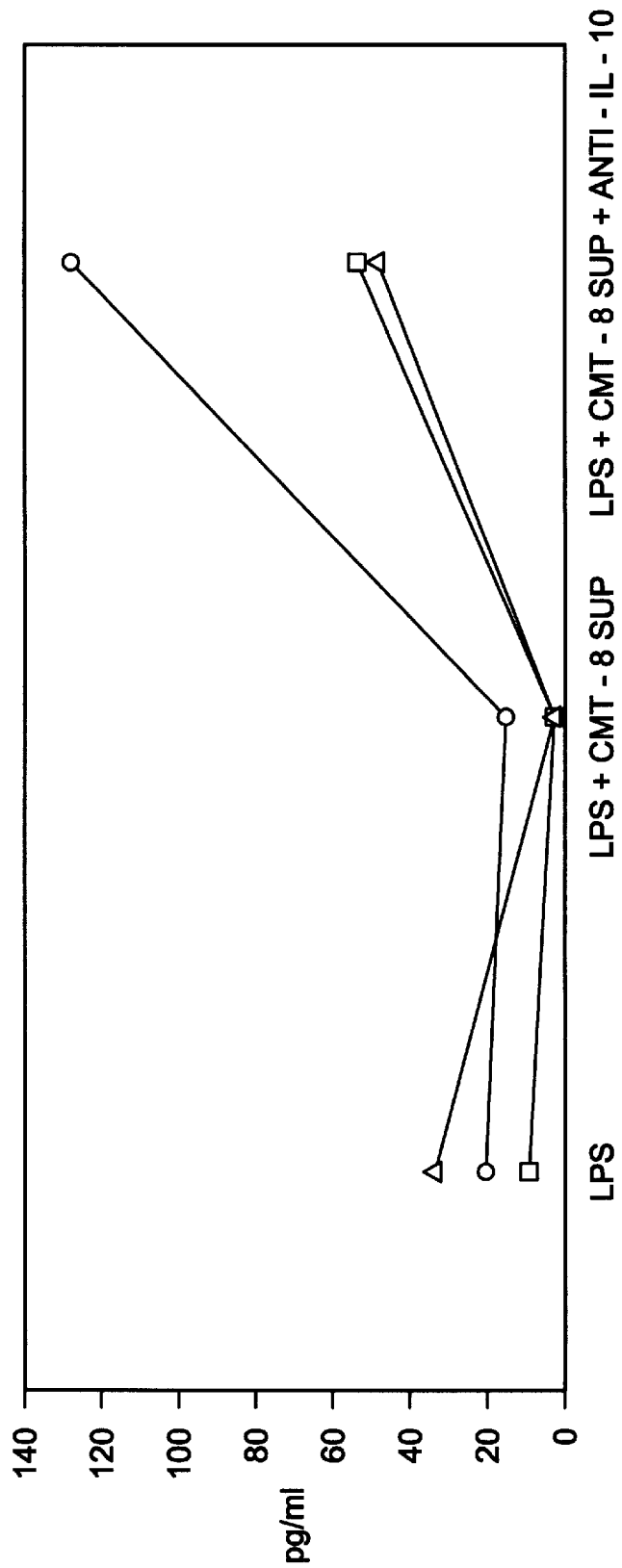

METHOD OF USING TETRACYCLINE COMPOUNDS TO ENHANCE INTERLEUKIN-10 PRODUCTION

This invention was made with Government support under R37 DE-03987, awarded by The National Institute of Dental Research. The Government has certain rights in the invention.

FIELD OF INVENTION

The present invention relates to a method of enhancing endogenous interleukin-10 (hereinafter IL-10) production in mammalian cells or tissues.

BACKGROUND OF THE INVENTION

Interleukins, interferons, colony stimulating factors and TNFα are examples of a group of diverse multi-functional proteins called cytokines. Cytokines are a class of secreted soluble proteins normally present in very low concentration in a variety of cells. Lymphoid, inflammatory hemopoietic and other cells such as connective tissue cells (e.g. fibroblasts, osteoblasts) secrete a variety of cytokines which regulate the immune, inflammatory, repair and acute phase responses by controlling cell proliferation, differentiation and effector functions. The effects of cytokines are mediated through binding to high affinity receptors on specific cell types. Collier et al., *Trends in Pharmacol. Sci.* 10: 427–431 (1989).

For example, the cytokine interleukin-1 (IL-1) is produced in cell types such as macrophages, synoviocytes, Iceratinocytes, chondrocytes and polymorphonuclear leukocytes. It is known to play a role in numerous conditions, in particular conditions accompanied by inflammation.

Several harmful effects are associated with increased IL-1. For example, in arthritis IL-1 stimulates synoviocytes associated with synovial hypertrophy. Further, IL-1 enhances cartilage matrix breakdown and inhibits cartilage repair by chondrocytes. This cytokine also induces bone resorption and thus may be involved in loss of bone density seen in rheumatoid arthritis. Weinblatt et al., *Journal of Rheumatology* 19:(Sup. 32):85–91(1992).

Excessive IL-1 production may cause fever, muscle wasting and drowsiness. For a review of the biological activities of IL-1, see Larrick, et al., *Immunology Today* 10:61–66 (1989). Thus, it is therapeutically desirable to inhibit the specific biological activity of IL-1.

One method of inhibiting IL-1 activity is by the use of systemic gene therapy. U.S. Pat. No. 5,766,585 discloses a method for treating rheumatoid arthritis inflammation and other autoimmune diseases in a mammal by administering a recombinant vector encoding an IL-1 antagonist.

TNFα is a cytokine that induces the production of IL-1. TNFα is a seventeen kDa peptide produced by activated macrophages as well as a wide variety of other cells during host immunological responses to microbial infections and neoplastic diseases. This cytokine is also recognized to be an important mediator of the inflammatory response. Beuller, et al., *Ann. Rev. Immunol.* 7: 625 (1989). It is therefore therapeutically desirable to inhibit the specific biological activity of TNFα as well as IL-1.

Another important cytokine is IL-10, a 35–40 kDa peptide produced by helper T-cells, B-cells, monocytes, macrophages and other cell types. In vitro, IL-10 has demonstrated immunosuppressive properties as evidenced by its ability to suppress cytokine production including IL-1 and TNFα (for a review, see Fiorentino et al., *Journal of Immunology* 147: 3815 (1991).

IL-10 also inhibits activation of other inflammatory cytokines, and therefore has potent anti-inflammatory activity. It is also known that IL-10 stimulates the proliferation of mast cells and thymocytes. Moore et al. "*Interleukin-10,*" *Annual Review in Immunology* 11: 165–190 (1993).

It has been of recent interest to administer IL-10 in the treatment of certain conditions characterized by excessive IL-1 and TNFα production. Such diseases or conditions include loosening of prosthetic joint implants, inflammation, diabetes, cancer, graft versus host diseases, viral, fungal and bacterial infections, lipopolysaccharide endotoxin shock, diseases of depressed bone marrow function, thrombocytopenia, osteoporosis, spondyloarthropathies, Paget's disease, inflammatory bowel disease, arthritis, osteoarthritis, autoimmune diseases such as rheumatoid arthritis, systemic lupus erythematosus, and connective tissue diseases.

For example, purified IL-10 has been shown in vitro to suppress certain types of viral infections. U.S. Pat. No. 5,665,345 discloses a method for inhibiting replication of the human immunodeficiency virus, retro-viruses, and Kaposi sarcoma in human cells by administering IL-10.

IL-10 has also been suggested for use in the treatment of certain cancers. U.S. Pat. No. 5,570,190 discloses administering exogenous IL-10 to treat mammals suffering from acute myelogenous leukemia and acute lymphocytic leukemia. IL-10 is said to be administered either in the purified or recombinant form and is believed to inhibit the proliferation of acute leukemia blast cells. However, there is an enormous expense associated with preparing a purified or recombinant parenteral form of IL-10.

Similarly, IL-10 was shown to inhibit bone marrow metastasis in severe combined immunodeficient mice. Stearns et al., *Invasion Metastasis* 17(2):62–74 (1997).

The above conventional approaches to treating conditions characterized by excessive IL-1 and TNFα production have been limited to administering exogenous purified or recombinant IL-10 intravenously. Since IL-10 is a protein, it is difficult to infuse intravenously into a mammal because proteins often leach out of solution and bind to the plastic or glass used in intravenous administration sets. Also, proteins are often incompatible and precipitate when mixed with physiological solutions such as dextrose or saline. In addition, oral and topical routes are unavailable for IL-10 administration. The oral route is unavailable because protein is degraded in the gastrointestinal tract.

None of the above approaches suggests enhancing endogenous IL-10 production in mammals for prophylaxis and treatment of diseases or conditions using compounds that are approved for use in humans and are available in the oral, injectable and topical routes.

The compound, tetracycline, exhibits the following general structure:

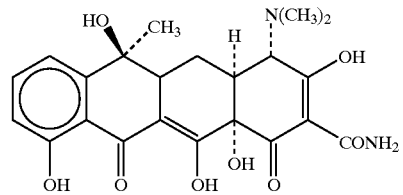

The numbering system of the ring nucleus is as follows:

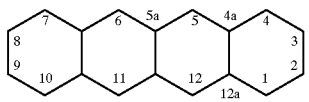

Tetracycline as well as the 5-OH (Terramycin) and 7-Cl (Aureomycin) derivatives exist in nature, and are well known antibiotics. Natural tetracyclines may be modified without losing their antibiotic properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antimicrobial activity. An example of a chemically modified tetracyclines (hereinafter CMT) is 4-dedimethylaminotetracyline which is commonly considered to be a non-antimicrobial tetracycline.

The use of tetracycline antibiotics, while effective, may lead to undesirable side effects. For example, the long-term administration of antibiotic tetracyclines may reduce or eliminate healthy flora, such as intestinal flora, and may lead to the production of antibiotic resistant organisms or the overgrowth of opportunistic yeast and fungi. These side-effects of long-term tetracycline therapy can be particularly disadvantageous to patients with diabetes because these patients are particularly susceptible to infection and impaired wound healing which might, at some future time, require antibiotic therapy to combat infection.

In addition to their antibiotic properties, tetracyclines have been described as having a number of other uses. For example, tetracyclines are also known to inhibit the activity of collagen destructive enzymes such as mammalian collagenase, gelatinase, macrophage elastase and bacterial collagenase. Golub et al., *J. Periodont. Res.* 20:12–23 (1985); Golub e t al. *Crit. Revs. Oral Biol Med.* 2: 297–322 (1991);U.S. Pat. Nos. 4,666,897; 4,704,383; 4,935,411; 4,935,412. In addition, tetracyclines have been known to inhibit wasting and protein degradation in mammalian skeletal muscle, U.S. Pat. No. 5,045,538.

Furthermore, tetracyclines have been shown to enhance bone protein synthesis in U.S. Pat. No. Re. 34,656, and to reduce bone resorption in organ culture in U.S. Pat. No. 4,704,383.

Similarly, U.S. Pat. No. 5,532,227 to Golub et al, discloses that tetracyclines can ameliorate the excessive glycosylation of proteins. In particular, tetracyclines inhibit the excessive collagen cross linking which results from excessive glycosylation of collagen in diabetes.

These properties cause the tetracyclines to be useful in treating a number of diseases. For example, there have been a number of suggestions that tetracyclines, including non-antimicrobial tetracyclines, are effective in treating arthritis. See, for example, Greenwald et al., "Tetracyclines Suppress Metalloproteinase Activity in Adjuvant Arthritis and, in Combination with Flurbiprofen, Ameliorate Bone Damage," *Journal of Rheumatology* 19:927–938(1992); Greenwald et al., "Treatment of Destructive Arthritic Disorders with MMP Inhibitors: Potential Role of Tetracyclines in, Inhibition of Matrix Metalloproteinases:Therapeutic Potential," *Annals of the New York Academy of Sciences* 732: 181–198 (1994); Kloppenburg et al., "Minocycline in Active Rheumatoid Arthritis," *Arthritis Rheum* 37:629–636(1994); Ryan et al., "Potential of Tetracycline to Modify Cartilage Breakdown in Osteoarthritis," *Current Opinion in Rheumatology* 8: 238–247(1996); O'Dell et al., "Treatment of Early Rheumatoid Arthritis with Minocycline or Placebo," *Arthritis Rheum* 40:842–848(1997).

Tetracyclines have also been suggested for use in treating skin diseases. For example, White et al., *Lancet, Apr.* 29, p. 966 (1989) report that the tetracycline minocycline is effective in treating dystrophic epidermolysis bullosa, which is a life-threatening skin condition believed to be related to excess collagenase.

The effectiveness of tetracycline in skin disorders has also been studied by Elewski et al., *Journal of the American Academy of Dermatology* 8:807–812 (1983). Elewski et al. disclosed that tetracycline antibiotics may have anti-inflammatory activity in skin diseases.

Similarly, Plewig et al., *Journal of Investigative Dermatology* 65:532 (1975), disclose experiments designed to test the hypothesis that antimicrobials are effective in treating inflammatory dermatoses. The experiments of Plewig et al. establish that tetracyclines have anti-inflammatory properties in treating pustules induced by potassium iodide patches.

The use of tetracyclines in combination with non-steroidal anti-inflammatory agents has been studied in the treatment of inflammatory skin disorders caused by acne vulgaris. Wong et al., *Journal of American Academy of Dermatology* 1: 1076–1081 (1984), studied the combination of tetracycline and ibuprofen and found that tetracycline was an effective agent against acne vulgaris while ibuprofen was useful in reducing the resulting inflammation by inhibition of cycloxygenase. Funt et al., *Journal of the American Academy of Dermatology* 13: 524–525 (1985), disclosed similar results by combining antimicrobial doses of minocycline with ibuprofen.

An antimicrobial tetracycline derivative, doxycycline, has been used to inhibit nitrate production. D'Agostiiio et al., *Journal of Infectious Diseases:* 177:489–92 (1998), disclose experiments where doxycycline, administered to mice injected with bacterial lipopolysaccharide (hereinafter LPS), exerted a protective effect by inhibiting nitrate production by an IL-10 independent mechanism. Experiments carried out in vitro also showed that doxycycline inhibited nitric oxide synthesis by LPS activated macrophages without enhancing endogenous IL-10 release. These data are contrary to the results of the present invention.

Based on the foregoing, tetracyclines have been found to be effective in different treatments. However, there has been no suggestion whatsoever that tetracyclines can be used to enhance endogenous production of IL-10.

Accordingly, it is one of the advantages of the present invention to overcome the above limitations of administering exogenous IL-10 and provide a method for enhancing endogenous IL-10 production in mammalian cells. Other advantages will readily present themselves to the skilled practitioner.

SUMMARY OF THE INVENTION

It has now been discovered that these and other objectives can be achieved by the present invention, which provides a method for enhancing endogenous interleukin-10 production in mammalian cells or tissues by administering to the cells an effective amount of a tetracycline derivative.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein:

FIG. 1 is a time series graph illustrating IL-10 production by LPS stimulated human peripheral blood macrophages in a dose-dependent response to CMT-3 (6-demethyl-6-deoxy-4-dedimethylaminotetracycline) and CMT-5 (tetracycline pyrazole).

FIG. 2 is a bar graph illustration of IL-10 production by human peripheral blood monocyte cells stimulated with IL-1, IL-10 CMT-5 (tetracycline pyrazole), IL-1+CMT-3 (6-demethyl-6-deoxy-4-dedimethylaminotetracycline) and IL-1+CMT-8 (6-α-deoxy-5-hydroxy-4-dedimethylaminotetracycline).

FIG. 3 is a bar graph illustration of IL-10 mRNA expression in third passage human synovial fibroblastoid cells in culture determined by northern blot analysis when stimulated with IL-1, IL-1+CMT-3 (6-demethyl-6-deoxy-4-dedimethylaminotetracycline), and IL-1+CMT-5 (tetracycline pyrazole).

FIG. 4 is a three dimensional dose-dependent response graph illustrating IL-10 production in human dermal fibroblasts cells, human synovial fibroblast cells, and human peripheral blood monocyte cells stimulated with IL-1, IL-1+CMT-5 (tetracycline pyrazole) and IL-1+CMT-3 (6-demethyl-6-deoxy-4-dedimethylaminotetracycline).

FIG. 5 is a graphic illustration of IL-10 biological activity as measured by the inhibition of cytokines TNFα and IL-1 in U937 and HL-60 cell cultures. Specifically, HL-60 cells were stimulated with LPS alone, then HL-60 cells were stimulated with supernatant from human peripheral blood monocyte cells which had IL-1+CMT-8 added. U937 cells were stimulated with LPS, then supernatant from human peripheral blood monocyte cells which had LPS+CMT-8 added. Quantities of TNFα and IL-1 produced were measured using ELISA. Endogenous TNFα and IL-1 production was increased when anti-IL-10 antibody was added to the U937 and HL60 cells.

DETAILED DESCRIPTION OF THE INVENTION

The method of the present invention is useful in enhancing endogenous IL-10 production, which is known to inhibit or down regulate IL-1 and TNFα production. As used herein, enhancing endogenous IL-10 production is defined as increasing or up-regulating IL-10 cytokine levels substantially over normal levels in vivo, within a mammal or in vitro, within mammalian cells or tissue. Preferably, endogenous IL-10 production is enhanced at least by from about 10% to about 1600% over normal levels. Up-regulating endogenous IL-10 results in the down regulation of cytokines IL-1 and TNFα.

The method of the present invention can be used in vivo, in vitro, and ex vivo, for example, in living mammals as well as in cultured tissue, organ or cellular systems. Mammals include, for example, humans, as well as pet animals such as dogs and cats, laboratory animals, such as rats and mice, and farm animals, such as horses and cows. Tissues, as used herein, are an aggregation of similarly specialized cells which together perform certain special functions. Cultured cellular systems include any cells that produce IL-10, such as human peripheral blood monocytes cells or synovial fibroblastoid cells.

In vivo practice of the invention permits application in the relief or palliation of medical and veterinary diseases, conditions, and syndromes. In particular, the method provides a means for protecting mammals suffering from diseases or other conditions associated with or mediated by increased or excessive IL-1 and TNFα production where it would be beneficial to enhance endogenous IL-10 production. Such conditions or diseases include but are not limited to inflammation, diabetes, cancer, graft versus host diseases, viral, fungal and bacterial infections, lipopolysaccharide endotoxin shock, diseases of depressed bone marrow function, thrombocytopenia, prosthetic joint loosening, osteoporosis, spondyloarthropathies, Paget's disease, inflammatory bowel disease, arthritis, osteoarthritis, autoimmune diseases such as rheumatoid arthritis, systemic; lupus erythematosus and connective tissue diseases.

A tetracycline derivative as used herein, exhibits the following general structure:

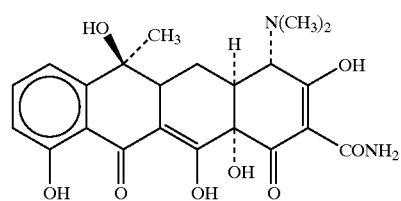

The numbering system of the multiple ring nucleus is as follows:

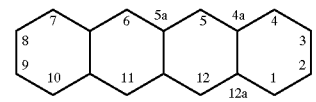

Tetracycline, as well as the 5-OH (oxytetracycline, e.g. Terramycin) and 7-Cl (chlorotetracycline, e.g., Aureomycin) derivatives, exist in nature, and are all well known antibiotics. Semisynthetic tetracyclines include, for example, doxycycline, minocycline and methacycline.

The use of tetracycline antibiotics, while generally effective for treating infection, can lead to undesirable side effects. For example, the long-term administration of antibiotic tetracyclines can reduce or eliminate healthy flora, such as intestinal flora, and can lead to the production of antibiotic resistant organisms or the overgrowth of yeast and fungi. These significant disadvantages typically preclude treatment regimens requiring chronic administration of these compounds.

A class of compounds has been defined which are structurally related to the antibiotic tetracyclines, but which have had their antibiotic activity substantially or completely eliminated by chemical modification. Substantial elimination of antibiotic activity occurs when the antibiotic activity is substantially less than that of tetracycline. Preferably, the antibiotic activity is at least approximately ten times less than that of tetracycline, and more preferably at least approximately five times less than that of tetracycline.

The modifications that may and may not be made to the basic tetracycline structure were reviewed by Mitscher, L. A., The Chemistry of the Tetracycline Antibiotics, Marcel Dekker, New York (1978), Ch. 6. According to Mitscher, the modification at positions 5–9 of the tetracycline ring system can be made without causing the complete loss of antibiotic properties. However, changes to the basic structure of the ring system, or replacement of substituents at positions 1–4 or 10–12, generally lead to synthetic tetracyclines with substantially less, or essentially no, antibacterial activity.

Chemically modified tetracyclines (CMT's) derivatives include, for example, 4-dedimethylaminotetracycline (CMT-1), tetracyclinonitrile (CMT-2), 6-demethyl-6-deoxy-4-dedimethylaminotetracycline (CMT-3), 7-chloro-4-dedimethylamino tetracycline (CMT-4), tetracyclinopyrazole (CMT-5), 4-hydroxy-4-dedimethylamiriotetracycline (CMT-6), 12 α-deoxy-4-dedimethylaminotetracycline (CMT-7), 5-hydroxy-6-α-deoxy-4-dedimethylaminotetracycline (CMT-8), 4-dedimethylamino-12-α-deoxyanhydrotetracycline (CMT-9), and 7-dimethylamino-6-demethyl-6-deoxy-4-dedimethylaminotetracycline (CMT-10). All are useful as non-antibacterial tetracyclines that enhance the endogenous production of IL-10.

Particularly preferred tetracycline derivatives suitable for use according to the present invention include 6-demethyl-6-deoxy 4-dedimethylaminotetracycline (CMT-3), 6-α-deoxy-5-hydroxy-4-dedimethylaminotetracycline (CMT-8), and tetracyclinopyrazole (CMT-5).

Tetracycline derivatives which possess antibacterial activity are also contemplated in the present invention. However, such compounds are preferably employed in an amount which has substantially no anti-bacterial activity but which is effective for enhancing the endogenous production of IL-10 in mammalian cells or tissues. Preferred compounds of this type include tetracycline, doxycycline, demeclocycline, and minocycline.

The chemically modified and anti-microbial tetracycline derivatives can be made by methods known in the art. See, for example, Mitscher, L. A., The Chemistry of the Tetracycline Antibiotics, Marcel Dekker, New York (1 978), Ch. 6, and U.S. Pat. Nos. 4,704,383 and 5,532,227.

In the method of the present invention, an effective amount of tetracycline derivative is administered. An effective amount as used herein is that amount effective to achieve the specified result of enhancing endogenous IL-10 production. Preferably, the tetracycline derivative is provided in an amount which has little or no antimicrobial activity. A tetracycline derivative is not effectively antimicrobial if it does not significantly prevent the growth of microbes. Accordingly, the method can beneficially employ a tetracycline derivative which has been modified chemically to reduce or eliminate its antimicrobial properties. The use of such chemically-modified tetracyclines is preferred in the present invention since they can be used at higher levels than antimicrobial tetracyclines, while avoiding certain disadvantages, such as the indiscriminate killing of beneficial microbes, and the emergence of resistant microbes, which often accompanies the use of antimicrobial or antibacterial amounts of such compounds.

Tetracycline derivatives useful according to the method of the invention appear to exhibit their beneficial effect in a dose-dependent manner. Thus, within broad limits, administration of larger quantities of a tetracycline derivative has been observed to enhance endogenous IL-10 production to a greater degree than does administration of smaller amounts. Moreover, efficacy has been observed at dosages below the level at which toxicity is seen.

Maximal dosage for a subject is the highest dosage which does not cause undesirable or intolerable side effects. For example, the tetracycline compound can be administered in an amount of from about 0.1 mg/kg/day to about 30 mg/kg/day, and preferably from about 1 mg/kg/day to about 18 mg/kg/day. For the purpose of the present invention, side effects may include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes without limitation dosages which are effective to achieve the described effect.

The method involves administering or providing a tetracycline derivative in an amount which is effective for enhancing IL-10 production in mammalian cells or tissue or in a mammal.

Administering the tetracycline derivatives can be accomplished in a variety of ways. In cultured cellular or tissue systems, tetracycline derivatives can be administered by contacting the cells or tissue directly with an effective amount of the tetracycline derivative.

In living mammals, tetracycline derivatives of the present invention can be administered systemically by the parenteral and enteral routes which also includes controlled release delivery systems. For example, tetracycline derivatives of the present invention can easily be administered intravenously (e.g., intravenous injection) which is a preferred route of delivery. Intravenous administration can be accomplished by mixing the tetracycline derivatives in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide the tetracycline derivative.

Alternatively, delivery of the tetracycline derivative can include topical application. Accordingly, the carrier is preferably suited for topical use. Compositions deemed to be suited for such topical use include gels, salves, lotions, creams, ointments and the like. The tetracycline derivative may also be incorporated with a support base or matrix or the like to provide a pre-packaged surgical or burn dressing or bandage which can be directly applied to skin. Topical application of tetracycline derivatives in amounts of up to about 25% (w/w) in a vehicle are therefore appropriate depending upon indication. More preferably, application of tetracycline derivatives in amounts of from about 0.1% to about 10% is believed to effectively enhance endogenous IL-10 production according to the invention. It is believed that these quantities do not induce significant toxicity in the subject being treated.

For example, in certain cases tetracycline compounds having only limited biodistribution may be preferred for localized activity. CMT-2, CMT-6, and other CMTs exhibiting such substantially local distribution are preferred for their localized efficacy in enhancing IL-10 activity at the site of injury, without exhibiting broader systemic inhibition. Topical application of these non-absorbable CMTs would be desirable in oral lesions, since the CMTs would not be absorbed to any significant degree even if swallowed.

Combined or coordinated topical and systemic administration of tetracycline derivatives is also contemplated under the invention. For example, a non-absorbable tetracycline compound, such as CMT-2 or CMT-6, can be administered topically, while a tetracycline compound capable of substantial absorption and effective systemic distribution in a subject, such as CMT-1, CMT-3, CMT-7, or CMT-8, can be administered systemically.

The invention has been developed based on the unexpected observation by Applicants that tetracycline derivatives enhance the endogenous production of the cytokine IL-10, which down-regulates the production and biological activity of IL-1 and TNF α. Applicants are also unaware of any physiological or biochemical basis for expecting that tetracyclines would enhance the endogenous production of IL-10 in systems capable of expressing IL-10. It is, therefore, surprising that tetracycline derivatives would be found to enhance endogenous IL-10 production.

The skilled artisan will appreciate the capacity of the examples below for demonstrating a method for enhancing endogenous interleukin-10 production in mammals. Accordingly, the results presented below clearly show that certain chemically modified tetracycline derivatives are capable of enhancing endogenous IL-10 production in mammalian cells or tissues. More generally, however, these derivatives can be utilized in other biological systems, and other diseases or conditions where it is desirable to enhance endogenous IL-10 production.

EXAMPLES

The following examples are provided to assist in a further understanding of the invention. The particular materials and conditions employed are intended to be further illustrative of the invention and are not limiting upon the reasonable scope thereof.

Example 1

Effects of Tetracyclines on LPS Stimulated Human Peripheral Blood Macrophages

Peripheral blood morocyte cells (PBMNC) obtained from healthy human blood donors were isolated from leukocyte concentrates by density gradient centrifugation over Lymphoprep (Nycomed, Oslo, Norway). Using the procedure of Levy and Edgington, *Journal of Experimental Medicine*, 151:1232 (1980), the cells were then plated and allowed to adhere to human serum coated plastic dishes. The cells were then detached with Puck's saline containing human serum albumin and EDTA and confirmed to be more than 90% mononuclear phagocytes by microscopic examination of cytospin preparations stained with modified Wright-Giemsa stain.

Culture Medium

The cells were then cultured for a minimum of 7 days in media containing RPMI 1640 medium (GIBCO; UK) supplemented with 10% human AB serum (NABI), 2 mMole/L glutamine, 1 mMole/L pyruvate, 25 mMole/L HEPES, 100 µg/ml streptomycin, and 20 µg/ml cefotaxime under nonadherent conditions in teflon beakers. PBMNC that differentiated into macrophages (monocyte-derived-macrophages) were harvested from the culture using the procedure of Liao et al., *Blood*, 83(8):2294–2304 (1994). The monocyte-derived-macrophages were resuspended in serum free medium at $1 \times 10^6$ cells per ml and plated onto well plates for various experiments. Conditioned media were collected and frozen at about minus 80° C. for subsequent analysis.

Viability of monocyte-derived-macrophages was assayed in the presence of various concentrations of CMTs from (about 5 µM to about 200 µM) by measuring the cells' ability to bioreduce the MTS tetrazolium compound [3-(4,5-dimethylthiaozol-2-yl)-5-(3-carboxymethoxyphenyl)-2-(4-sulfophenyl)-2H-tetrazolium] into a colored formazan product (Promega, Madison, Wis.). It was noted that there were no significant cytotoxic effects on the cells with CMTs concentrations of 5 µM and 10 µM.

Conditioned media

The conditioned media contained macrophage cultures with the following additives: (a) no bacterial LPS; (b) bacterial LPS (which is known to enhance the production of IL-1, TNFα, and IL-10) at 0.2 µg/ml; (c) bacterial LPS at 0.2 µg/ml+CMT-3 (a tetracycline derivative having a high level of anti-collagenase activity) at 5 µM; (d) bacterial LPS at 0.2 µg/ml +CMT-5 (a tetracycline derivative having no appreciable anti-collagenase activity) at 10 µM; (e) bacterial LPS at 0.2 µg/ml+CMT-3 at 10 µM; (f) bacterial LPS at 0.2 µg/ml+CMT-3 at 20 µM.

The conditioned media were analyzed for endogenous IL-10 production at 2, 4, 8 and 24 hours after incubation of the macrophages in cell culture, using an ELISA kit (Endogen, Inc., Woburn, Mass.) that incorporates a monoclonal antibody which binds human IL-10.

The results are shown graphically in FIG. 1. Culturing the macrophages without LPS did not result in the production of any detectable endogenous IL-10. However, administering 0.2 µg/ml of LPS to the macrophages in culture dramatically stimulated endogenous IL-10 production to about 180 pg/ml (picograms/ml) after six hours and to about 230 pg/ml at the end of 24 hours.

Administering CMT-3 to the LPS-stimulated macrophages (but not to the macrophages in the absence of LPS) increased the IL-10 production, in a dose-dependent manner beyond the elevated levels produced by LPS alone. Increasing the dosage amount to about 5 µM of CMT-3 did not increase the level of endogenous IL-10 production. After 8 hours, dosages of 10 µM and 20 µM CMT-3 increased endogenous IL-10 production by from about 50% to about 100%, respectively, beyond the level of IL-10 produced by LPS alone.

Similarly, 10 µM of CMT-3 and 20 µM of CMT-3 continued to increase endogenous IL-10 production to about 380 pg/ml and about 400 pg/ml respectively, at the end of 24 hours. CMT-5 at 10 µM dosages produced the same increase in endogenous IL-10 production as 10 µM of CMT-3, at the 8 hour time period. This represents an increase from about 50% to about 100% in endogenous IL-10 production beyond the level of IL-10 produced by LPS alone. However, CMT-5 at 10 µM did not continue to increase endogenous IL-10 production, like CMT-3, with longer incubation periods of 24 hours.

Example 2

Effects of Tetracyclines on IL-1 Stimulated Human Peripheral Blood Monocyte Cells Human PBMNC obtained from healthy human blood donors were freshly isolated from leukocyte concentrates by density gradient centrifugation over Ficoll-Paque (Pharmacia, U.S.).

Culture Medium

The cells were then cultured in media containing RPMI 1640 medium (GIBCO, UK) supplemented with 1% FBS (Fetal Bovine Serum), 2 mMole/L glutamine, 100 µg/ml streptomycin, and 100 units penicillin in 24 well tissue culture plates. PBMNC were re-suspended in serum free medium at $1 \times 10^6$ cells per ml and plated onto well plates for various experiments. Conditioned media were collected and frozen at about minus 20° C. for subsequent analysis.

Conditioned media

The conditioned media contained PBMNC cultures with the following additives: (a) no IL-1; (b) IL-1 at 1 ng/ml; (c) IL-1 at 1 ng/ml+CMT-5 (tetracycline pyrazole) at 5 µg/ml; (d) IL-1 at 1 ng/ml+CMT-3 at 5 µg/ml; and (e) IL-1 at 1 ng/ml+CMT-8 at 5 µg/ml.

The conditioned media were analyzed for endogenous IL-10 production after a 48 hour incubation period using ELISA (Endogen, Inc., Woburn, Mass.) that incorporated a monoclonal antibody which binds human IL-10.

FIG. 2 is a bar graph illustration of IL-10 production by human PBMNC. Culturing the mononuclear cells without IL-1, with IL-1, or with IL-1+CMT-5 did not result in the production of any detectable endogenous IL-10. However, the culture with 1 ng/ml of IL-1+5 µg/ml of CMT-3 produced endogenous IL-10 in an amount up to about 160 pg/ml at the end of 48 hours. Similarly, the culture with IL-1+5 µg/m of CMT-8 added to the mononuclear cells increased the endogenous production of IL-10 up to about 180 pg/ml. This represents up to about a sixteen fold increase in endogenous IL-10 production.

Example 3

Effects of Tetracyclines on IL-1 Stimulated Human Synovial Fibroblastoid Cells

Human synovial fibroblastoid cells (SF) were cultured in media containing 1% FBS in DMEM medium supplemented with 2 mMole/L glutamine, 100 µg/ml streptomycin, and 100 units penicillin in 150 cm$^2$ tissue culture flasks. The culture further contained: (a) IL-1 at 1 ng/ml; (b) IL-1 at 1 ng/ml+CMT-5 at 5 µg/ml; (c) IL-1 at 1 ng/ml+CMT-3 at 5 µg/ml; and (d) the control which was CMT-5 at 5 µg/ml. Cells were incubated for a 48 hour period. Messenger RNA was isolated and IL-10 production was analyzed by northern blot analysis.

Referring to FIG. 3, endogenous IL-10 mRNA expression or production is shown graphically based on the absorbency units using northern blot analysis. CMT-3 dramatically enhanced endogenous IL-10 production in SF cells represented by the increase in absorbency units. Referring to FIG. 4, production of endogenous IL-10 in SF cells was up to about 25 pg/ml. No increase in endogenous IL-10 production was noted for cells stimulated with IL-1+CMT-5. These results clearly show that certain chemically modified tetracycline derivatives are capable of enhancing endogenous IL-10 production in SF cells.

Example 4

Effect of Tetracyclines on IL-10 Production in IL-1 Stimulated Dermal Fibroblastoid Cells Dermal Fibroblast cells (DF) were cultured in media containing 1% FBS in DMEM medium supplemented with 2 mMole/L glutamine, 100 µg/ml streptomycin, and 100 units penicillin in 150 cm$^2$ tissue culture flasks. The culture further contained: (a) no additives; (b) IL-1 at 1 ng/ml; (c) IL-1 at 1 ng/ml +CMT-5 at 5 µg/ml; and (d) IL-1 at 1 ng/ml+CMT-3 at 5 µg/ml. Endogenous IL-10 production was measured using ELISA (Endogen, Inc., Woburn, Mass.) that incorporated a monoclonal antibody which binds human IL-10. Cultures were incubated for 48 hours.

DF cells exhibited no endogenous production of IL-10 when IL-1 and CMT-3 were added. Similar results w ere exhibited by DF cells when IL-1+CMT-5 were added. These data demonstrate that DF cells do not produce endogenous IL-10. These results are shown graphically in FIG. 4 which is a three-dimensional graph summarizing the endogenous IL-10 production in human DF cells, human SF cells, and human PBMNC stimulated with IL-1, IL-1+CMT-5 and IL-1+CMT-3.

Example 5

The next experiment was designed to determine if the endogenous IL-10 produced was biologically active. Biological activity of endogenous IL-10 was measured by its ability to inhibit cytokines TNF-α and IL-1 production in two indicator cell lines U937 (ATCC, accession number CRL 1593, Rockville, Md.) and HL-60 (ATCC, accession number CCL 240, Rockville, Md.). These cell lines were cultured ($1\times10^6$ cells/ml ) in 1 ml flat bottom wells. To generate the supernatant used in the experiment, PBMNC were stimulated with 1 ng/ml of IL-1+5 µg/ml of CMT-8 and incubated for 48 hours. This supernatant contained 1.23 µg/ml of IL-10. Cell line HL-60 was cultured with: (a) 5 µg/ml of LPS; (b) 5 µg/ml of LPS+20% supernatant from PBMNC treated with 5 µg/ml of CMT-8; (c) 5 µg/ml of LPS+20% supernatant from PBMNC treated with 5 µg/ml of CMT-8+anti-IL-10 antibodies (Endogen, Inc., Woburn, Mass.). U937 cells were cultured with: (a) 5 µg/ml of LPS; (b) 5 µg/ml of LPS+20% supernatant from PBMNC treated with 5 µg/ml of CMT-8; (c) 5 µg/ml of LPS+20% supernatant from PBMNC treated with 5 µg/ml of CMT-8+anti-IL-10 antibodies.

FIG. 5 is a graphic illustration of IL-10 biological activity as measured by the inhibition of cytokines TNFα and IL-1 in U937 and HL-60 cell cultures. Endogenous TNF-α and IL-1 production was measured by ELISA assaying the amount of cytokine produced in pg/mi. Supernatant (sup) from CMT-8 stimulated PBMNC down-regulated endogenous TNF-α and IL-1 production in U937 and HL-60 cells. This effect was blocked by anti-IL-10 antibody (anti-IL-10). These data clearly show that certain chemically modified tetracycline derivatives enhance the production of endogenous IL-10 which inhibits or down-regulates IL-1 and TNFα production.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method for enhancing endogenous interleukin-10 production in mammalian cells or tissues, which comprises administering to said cells an effective amount of a tetracycline derivative.

2. The method in accordance with claim 1 wherein said tetracycline derivative has substantially no effective antimicrobial activity.

3. The method in accordance with claim 1 wherein said tetracycline derivative is a 4-dedimethylaminotetracycline.

4. The method in accordance with claim 1 wherein said mammalian cells or tissue are in a mammal.

5. The method in accordance with claim 3 wherein said tetracycline derivative is 6-demethyl-6-deoxy-4-dedimethylaminotetracycline.

6. The method in accordance with claim 3 wherein said tetracycline derivative is tetracyclino-pyrazole.

7. The method in accordance with claim 3 wherein said tetracycline derivative is 7-chloro-4-dedimethylaminotetracycline.

8. The method in accordance with claim 3 wherein said tetracycline derivative is 4-hydroxy-4-dedimethylaminotetracycline.

9. The method in accordance with claim 3 wherein said tetracycline derivative is 12α-deoxy-4-dedimethylaminotetracycline.

10. The method in accordance with claim 3 wherein said tetracycline derivative is 5-hydroxy-6-α-deoxy-4-dedimethylaminotetracycline.

11. The method in accordance with claim 3 wherein said tetracycline derivative is 4-dedimethylamino-12α-deoxyanhydrotetracycline.

12. The method in accordance with claim 3 wherein said tetracycline derivative is 7-dimethylamino-6-demethyl-6-deoxy-4-dedimethylaminotetracycline.

13. The method in accordance with claim 1 wherein said tetracycline derivative is tetracyclinonitrile.

14. The method in accordance with claim 1 wherein said tetracycline derivative is an antimicrobial tetracycline.

15. The method in accordance with claim 14 wherein said tetracycline derivative is tetracycline.

16. The method in accordance with claim 14 wherein said tetracycline derivative is minocycline.

17. The method in accordance with claim 14 wherein said tetracycline derivative is doxycycline.

18. The method in accordance with claim 1 wherein said tetracycline derivative is administered orally.

19. The method in accordance with claim 1 wherein said tetracycline derivative is administered systemically.

20. The method in accordance with claim 1 wherein said tetracycline derivative is administered topically.

21. The method in accordance with claim 19 wherein said tetracycline derivative is administered systemically by a controlled release delivery system.

* * * * *